US012703677B2

(12) United States Patent
Wakabayashi et al.

(10) Patent No.: US 12,703,677 B2
(45) Date of Patent: Aug. 11, 2026

(54) (METH)ACRYLIC ACID ESTER COMPOUND HAVING ISOCYANATE GROUP AND METHOD FOR PRODUCING SAME

(71) Applicant: SHOWA DENKO K.K., Tokyo (JP)

(72) Inventors: Tomomitsu Wakabayashi, Tokyo (JP); Yoshihiko Maeda, Tokyo (JP)

(73) Assignee: Resonac Corporation, Tokyo (JP)

( * ) Notice: Subject to any disclaimer, the term of this patent is extended or adjusted under 35 U.S.C. 154(b) by 1000 days.

(21) Appl. No.: 17/790,415

(22) PCT Filed: Jan. 4, 2021

(86) PCT No.: PCT/JP2021/000012

§ 371 (c)(1), (2) Date: Jun. 30, 2022

(87) PCT Pub. No.: WO2021/141002

PCT Pub. Date: Jul. 15, 2021

(65) Prior Publication Data

US 2023/0056109 A1 Feb. 23, 2023

(30) Foreign Application Priority Data

Jan. 6, 2020 (JP) ................................ 2020-000234

(51) Int. Cl.
*C07C 263/10* (2006.01)
*C07C 263/16* (2006.01)

(52) U.S. Cl.
CPC .......... *C07C 263/10* (2013.01); *C07C 263/16* (2013.01)

(58) Field of Classification Search
None
See application file for complete search history.

(56) References Cited

U.S. PATENT DOCUMENTS

2005/0277788 A1* 12/2005 Job ........................ C07C 51/60 562/857
2007/0197762 A1 8/2007 Nozawa et al.
2013/0023694 A1* 1/2013 Steiger .................. C07C 263/08 560/222
2013/0317252 A1* 11/2013 Nishimura ............ C07C 263/18 560/331

FOREIGN PATENT DOCUMENTS

| | | | |
|---|---|---|---|
| CN | 1934075 | A | 3/2007 |
| CN | 101142252 | A | 3/2008 |
| CN | 102702028 | A | 10/2012 |
| CN | 102844297 | A | 12/2012 |
| CN | 103113261 | A | 5/2013 |
| CN | 103193675 | A | 7/2013 |
| CN | 103370303 | A | 10/2013 |
| CN | 103380106 | A | 10/2013 |
| CN | 104086458 | A | 10/2014 |
| CN | 109843963 | A | 6/2019 |
| EP | 0 346 756 | A1 | 12/1989 |
| JP | 54-5921 | A | 1/1979 |
| JP | 64-42461 | A | 2/1989 |
| JP | 64-42462 | A | 2/1989 |
| JP | 64-42463 | A | 2/1989 |
| JP | 7-278088 | A | 10/1995 |
| JP | 2005-60392 | A | 3/2005 |
| JP | 2006-232797 | A | 9/2006 |
| JP | 2006-291188 | A | 10/2006 |
| JP | 2007-55993 | A | 3/2007 |
| JP | 2013-523881 | A | 6/2013 |
| JP | 2014-62071 | A | 4/2014 |
| JP | 2014-234376 | A | 12/2014 |
| JP | 2016-150922 | A | 8/2016 |
| KR | 10-2007-0119687 | A | 12/2007 |
| TW | 201329115 | A | 7/2013 |
| WO | 2006/103979 | A1 | 10/2006 |
| WO | 2008/143207 | A1 | 11/2008 |
| WO | 2018/070541 | A1 | 4/2018 |

OTHER PUBLICATIONS

L. F. Fieser, et al., "N-Methylformanilide [Formanilide, N-methyl-]", Organic Syntheses, Coll., 1940, vol. 20, p. 66 (3 pages total).
M. Bloemendal, et al., "Enthalpic Interaction Coefficients of Formamides Dissolved in N,N-Dimethylformamide", Journal of Solution Chemistry, 1986, vol. 15, No. 1, pp. 81-96 (16 pages).
STN Cas No. 13641-96-8, "2-Propenoic acid, 2-isocyanatoethyl ester", Registry, Nov. 16, 1984 (1 page total).
STN Cas No. 30674-80-7, "2-Propenoic acid, 2-methyl-, 2-isocyanatoethyl ester", Registry, Nov. 16, 1984 (1 page total).
STN Cas No. 107023-60-9, "2-Propenoic acid, 2-methyl-, 2-(2-isocyanatoethoxy)ethyl ester", Registry, Mar. 14, 1987 (1 page total).

(Continued)

*Primary Examiner* — Amy C Bonaparte
(74) *Attorney, Agent, or Firm* — Sughrue Mion, PLLC

(57) ABSTRACT

The objective of the present invention is to reduce the content of dialkylcarbamoyl chloride contained in a (meth) acrylic acid ester compound having an isocyanate group. The present invention includes a method for producing a (meth)acrylic acid ester compound having an isocyanate group in which the content of dialkylcarbamoyl chloride is 0.1 mass % or less, where the method includes a step (2) in which a predetermined compound (B) and phosgene are brought into contact in the presence of an N-disubstituted formamide compound (A) to obtain a phosgene reaction product, and a step (3) in which the phosgene reaction product obtained in step (2) and a hydroxylamine hydrochloride compound are brought into contact to obtain a (meth)acrylic acid ester compound having a predetermined isocyanate group.

6 Claims, No Drawings

(56) References Cited

OTHER PUBLICATIONS

STN Cas No. 886577-76-0, "2-Propenoic acid, 1,11-(2-isocyanato-2-methyl-1,3-propanediyl) ester", Registry, Jun. 2, 2006 (1 page total).
STN Cas No. 1088364-03-7, "2-Propenoic acid, 2-(2-isocyanatoethoxy)ethyl ester", Registry, Dec. 22, 2008 (1 page total).

* cited by examiner

(METH)ACRYLIC ACID ESTER COMPOUND HAVING ISOCYANATE GROUP AND METHOD FOR PRODUCING SAME

CROSS REFERENCE TO RELATED APPLICATIONS

This application is a National Stage of International Application No. PCT/JP2021/000012, filed on Jan. 4, 2021, which claims priority from Japanese Patent Application No. 2020-000234, filed on Jan. 6, 2020.

TECHNICAL FIELD

The present invention relates to a (meth)acrylic acid ester compound having an isocyanate group and a method for producing the same.

BACKGROUND ART

A (meth)acrylic acid ester compound having an isocyanate group, as represented by acryloyloxyethyl isocyanate and methacryloyloxyethyl isocyanate, is utilized in materials such as paints (coating materials), adhesives, photoresists, dental materials, and magnetic recording materials, and is a very industrially useful compound, because such compounds have an ethylenic double bond per molecule with the highly reactive isocyanate group.

A (meth)acrylic acid ester compound having an isocyanate group can be produced, for example, by means of a compound such as a (meth)acrylic acid compound and phosgene in the presence of a catalyst (refer to Patent Literature 1).

In the production of a (meth)acrylic acid ester compound having an isocyanate group by means of phosgene, when utilizing N,N-dimethylformamide (hereunder referred to as 'DMF') as a catalyst for performing acid-chlorination of a (meth)acrylic acid compound which is a raw material, the phosgene and DMF react, and dimethylcarbamoyl chloride (DMCC), which is a dialkylcarbamoyl chloride, is generated as an impurity. DMCC is highly toxic, and also reacts violently with water to generate hydrochloric acid vapor. Furthermore, as the dialkylcarbamoyl chloride decomposes, hydrogen chloride and dialkyl amines are generated, which promote, for example, the corrosion of metals.

CITATION LIST

Patent Literature

Patent Literature 1: JP S54-005921 A

SUMMARY OF INVENTION

Technical Problem

In order to remove the dialkylcarbamoyl chloride contained in a (meth)acrylic acid ester compound having an isocyanate group, refining treatment such as distillation is performed. However, in regards to the means to reduce the content of dialkylcarbamoyl chloride contained in a (meth) acrylic acid ester compound, there was still room for improvement.

Taking the aforementioned problem into consideration, the objective of the present invention is to reduce the content of dialkylcarbamoyl chloride contained in a (meth)acrylic acid ester compound.

Solution to Problem

As a result of keen investigation of the aforementioned problem by the present inventors, it was discovered that when reacting a compound having an ethylenically unsaturated group which is a raw material, with phosgene, the content of dialkylcarbamoyl chloride contained in a (meth) acrylic acid ester compound having an isocyanate group could be reduced by means of a predetermined catalyst, and the completion of the present invention was thereby achieved. Namely, the present invention comprises the matters according to, for example, the below [1] to [18].

[1] A method for producing a (meth)acrylic acid ester compound having an isocyanate group, in which the content of dialkylcarbamoyl chloride is 0.1 mass % or less in the (meth)acrylic acid ester compound having an isocyanate group, where the method includes:

a step (2) in which a compound (B) expressed by the following formula (2) and phosgene are brought into contact in the presence of an N-disubstituted formamide compound (A) to obtain a phosgene reaction product;

and a step (3) in which the phosgene reaction product obtained in the step (2) and a hydroxylamine hydrochloride compound are brought into contact to obtain a (meth)acrylic acid ester compound having an isocyanate group expressed by the following formula (1).

$$R^3\text{—CO—OH} \quad (2)$$

(in formula (2), $R^3$ is an ethylenically unsaturated group having 2 or 3 carbon atoms)

$$(R^3\text{—COO})_n\text{—}R^4\text{—}(NCO)_m \quad (1)$$

(in formula (1), $R^1$ means the same as that of the aforementioned formula (2), $R^4$ is a (m+n)-valent hydrocarbon group having 1 to 7 carbon atoms and may optionally contain an ether group, and m and n each independently represent an integer of 1 or 2)

[2] The method for producing the (meth)acrylic acid ester compound having an isocyanate group according to [1], in which the dialkylcarbamoyl chloride is at least one kind of compound selected from the group consisting of N,N-dimethylcarbamoyl chloride, dihexylcarbamoyl chloride, dibenzylcarbamoyl chloride, dicyclohexylcarbamoyl chloride and di-(2-ethylhexyl)carbamoyl chloride.

[3] The method for producing the (meth)acrylic acid ester compound having an isocyanate group according to [1] or [2], in which the compound (A) is dihexyl formamide, dibenzyl formamide, dicyclohexyl formamide or di(2-ethylhexyl)formamide.

[4] The method for producing the (meth)acrylic acid ester compound having an isocyanate group according to any of [1] to [3], in which the (meth)acrylic acid ester compound having an isocyanate group is 2-acryloyloxyethyl isocyanate, 2-methacryloyloxyethyl isocyanate, 2-(isocyanate ethyloxy)ethyl acrylate, 2-(isocyanate ethyloxy)ethyl methacrylate or 1,1-bis (acryloyloxymethyl)ethyl isocyanate.

[5] The method for producing the (meth)acrylic acid ester compound having an isocyanate group according to any of [1] to [4], in which the content of dialkylcarbamoyl chloride in the (meth)acrylic acid ester compound having an isocyanate group is 1 mass ppm or more.

[6] The method for producing the (meth)acrylic acid ester compound having an isocyanate group according to any of [1] to [5], where the method further includes a step (1) in which a compound (E) expressed by the following formula (3) and formic acid are brought into contact to obtain the compound (A).

$$NHR^1R^2 \quad (3)$$

(in the formula, $R^1$ and $R^2$ are each independently an alkyl group having 5 to 10 carbon atoms which may have substituents, a cycloalkyl group having 5 to 10 carbon atoms which may have substituents, or an aryl group having 6 to 10 carbon atoms which may have substituents)

[7] The method for producing the (meth)acrylic acid ester compound having an isocyanate group according to any of [1] to [6], in which the content of the N-disubstituted formamide compound (A) is 100 mass ppm or less.

[8] A (meth)acrylic acid ester compound having an isocyanate group expressed by the following formula (1), in which the content of dialkylcarbamoyl chloride is 0.1 mass % or less.

$$(R^3\text{—COO})_n\text{—}R^4\text{—}(NCO)_m \quad (1)$$

(in formula (1), $R^3$ is an ethylenically unsaturated group having 2 or 3 carbon atoms, $R^4$ is a (m+n)-valent hydrocarbon group having 1 to 7 carbon atoms and may optionally contain an ether group, and m and n each independently represent an integer of 1 or 2)

[9] The (meth)acrylic acid ester compound having an isocyanate group according to (8), in which the dialkylcarbamoyl chloride is at least one kind of compound selected from the group consisting of N,N-dimethylcarbamoyl chloride, dihexylcarbamoyl chloride, dibenzylcarbamoyl chloride, dicyclohexylcarbamoyl chloride and di-(2-ethylhexyl)carbamoyl chloride.

[10] The (meth)acrylic acid ester compound having an isocyanate group according to [8] or [9], in which the (meth)acrylic acid ester compound having an isocyanate group is 2-acryloyloxyethyl isocyanate, 2-methacryloyloxyethyl isocyanate, 2-(isocyanate ethyloxy)ethyl acrylate, 2-(isocyanate ethyloxy)ethyl methacrylate or 1,1-bis(acryloyloxymethyl)ethyl isocyanate.

[11] The (meth)acrylic acid ester compound having an isocyanate group according to any of [8] to [10], in which the content of dialkylcarbamoyl chloride in the (meth)acrylic acid ester compound having an isocyanate group is 1 mass ppm or more.

[12] The (meth)acrylic acid ester compound having an isocyanate group according to any of [8] to [11], in which the content of the N-disubstituted formamide compound (A) in the (meth)acrylic acid ester compound having an isocyanate group is 100 mass ppm or less.

[13] A (meth)acrylic acid ester compound having an isocyanate group expressed by the following formula (1), in which the content of dialkylcarbamoyl chloride is 0.1 mass % or less, and in which a compound (B) expressed by the following formula (2) and phosgene are brought into contact in the presence of an N-disubstituted formamide compound (A) to obtain a phosgene reaction product, and the resultant phosgene reaction product and a hydroxylamine hydrochloride compound are brought into contact to obtain the (meth) acrylic acid ester compound having an isocyanate group.

$$R^3\text{—CO—OH} \quad (2)$$

(in formula (2), $R^3$ is an ethylenically unsaturated group having 2 or 3 carbon atoms)

$$(R^3\text{—COO})_n\text{—}R^4\text{—}(NCO)_m \quad (1)$$

(in formula (1), $R^1$ means the same as that of the aforementioned formula (2), $R^4$ is a (m+n)-valent hydrocarbon group having 1 to 7 carbon atoms and may optionally contain an ether group, and m and n each independently represent an integer of 1 or 2)

[14] The (meth)acrylic acid ester compound having an isocyanate group according to [13], in which the dialkylcarbamoyl chloride is at least one kind of compound selected from the group consisting of N,N-dimethylcarbamoyl chloride, dihexylcarbamoyl chloride, dibenzylcarbamoyl chloride, dicyclohexylcarbamoyl chloride and di-(2-ethylhexyl)carbamoyl chloride.

[15] The (meth)acrylic acid ester compound having an isocyanate group according to [13] or [14], in which the compound (A) is dihexyl formamide, dibenzyl formamide, dicyclohexyl formamide or di(2-ethylhexyl)formamide.

[16] The (meth)acrylic acid ester compound having an isocyanate group according to any of [13] to [15], in which the (meth)acrylic acid ester compound having an isocyanate group is 2-acryloyloxyethyl isocyanate, 2-methacryloyloxyethyl isocyanate, 2-(isocyanate ethyloxy)ethyl acrylate, 2-(isocyanate ethyloxy)ethyl methacrylate or 1,1-bis(acryloyloxymethyl)ethyl isocyanate.

[17] The (meth)acrylic acid ester compound having an isocyanate group according to any of [13] to [16], in which the content of dialkylcarbamoyl chloride in the (meth)acrylic acid ester compound having an isocyanate group is 1 mass ppm or more.

[18] The (meth)acrylic acid ester compound having an isocyanate group according to any of [13] to [17], in which the content of the N-disubstituted formamide compound (A) is 100 mass ppm or less in the (meth) acrylic acid ester compound having an isocyanate group.

Advantageous Effects of Invention

The (meth)acrylic acid ester compound having an isocyanate group of the present invention is useful in fields such as paints (coating materials), adhesives, photoresists, dental materials and magnetic recording materials, because of the low content of dialkylcarbamoyl chloride which is an impurity.

DESCRIPTION OF EMBODIMENTS

The present invention includes a (meth)acrylic acid ester compound having an isocyanate group in which the content of dialkylcarbamoyl chloride is 0.1 mass % or less, and a method for producing the same. The present invention will be explained in detail below. In the present invention, '(meth)acrylic acid' means methacrylic acid or acrylic acid.

<(Meth)Acrylic Acid Ester Compound Having an Isocyanate Group>

A (meth)acrylic acid ester compound having an isocyanate group in which the content of dialkylcarbamoyl chloride is 0.1 mass % or less, which is an embodiment of the present invention, will be explained.

In the present invention, the (meth)acrylic acid ester compound having an isocyanate group (—NCO) is expressed by the following formula (1).

$$(R^3\text{—COO})_n\text{—}R^4\text{—(NCO)}_m \quad (1)$$

In formula (1), $R^3$ is an ethylenically unsaturated group having 2 or 3 carbon atoms. If $R^3$ has 4 or more carbon atoms, the reactivity of the ethylenically unsaturated group may deteriorate. $R^3$ is preferably $CH_2{=}CH(CH_3)$— or $CH_2{=}CH_2$— (vinyl group), from the perspective of the raw material being easily obtainable.

In formula (1), $R^4$ is a (m+n)-valent hydrocarbon group having 1 to 7 carbon atoms, preferably 2 to 6, more preferably 3 to 5, and further preferably 2 carbon atoms, and may be linear or branched. $R^4$ may further contain an ether bond. $R^4$ is preferably —$CH_2$—, —$CH_2CH_2$—, or —$CH_2CH_2OCH_2CH_2$—, and more preferably —$CH_2CH_2$—, from the perspective of the raw material being easily obtainable.

In formula (1), m and n each independently represent an integer of 1 or 2, and either preferably are 1, from the perspective of easy production.

Examples of the (meth)acrylic acid ester compound having an isocyanate group expressed in formula (1) include, e.g., 2-methacryloyloxyethyl isocyanate, 3-methacryloyloxy-n-propyl isocyanate, 2-methacryloyloxy isopropyl isocyanate, 4-methacryloyloxy-n-butyl isocyanate, 2-methacryloyloxy-tert-butyl isocyanate, 2-methacryloyloxy butyl-4-isocyanate, 2-methacryloyloxy butyl-3-isocyanate, 2-methacryloyloxy butyl-2-isocyanate, 2-methacryloyloxy butyl-1-isocyanate, 5-methacryloyloxy-n-pentyl isocyanate, 6-methacryloyloxy-n-hexyl isocyanate, 7-methacryloyloxy-n-heptyl isocyanate, 2-(isocyanate ethyloxy)ethyl methacrylate, 3-methacryloyloxy phenyl isocyanate, 4-methacryloyloxy phenyl isocyanate, 2-acryloyloxyethyl isocyanate, 3-acryloyloxy-n-propyl isocyanate, 2-acryloyloxy isopropyl isocyanate, 4-acryloyloxy-n-butyl isocyanate, 2-acryloyloxy-tert-butyl isocyanate, 2-acryloyloxy butyl-4-isocyanate, 2-acryloyloxy butyl-3-isocyanate, 2-acryloyloxy butyl-2-isocyanate, 2-acryloyloxy butyl-1-isocyanate, 5-acryloyloxy-n-pentyl isocyanate, 6-acryloyloxy-n-hexyl isocyanate, 7-acryloyloxy-n-heptyl isocyanate, 2-(isocyanate ethyloxy)ethyl acrylate, 3-acryloyloxy phenyl isocyanate, 4-acryloyloxy phenyl isocyanate, 1,1-bis(methacryloyloxymethyl)methyl isocyanate, 1,1-bis (methacryloyloxymethyl)ethyl isocyanate, 1,1-bis (acryloyloxymethyl)methyl isocyanate, and 1,1-bis (acryloyloxymethyl)ethyl isocyanate.

Among these, from the perspective of easy production and/or the raw material being easily obtainable, 2-acryloyloxyethyl isocyanate, 2-methacryloyloxyethyl isocyanate, 2-(isocyanate ethyloxy)ethyl acrylate, 2-(isocyanate ethyloxy)ethyl methacrylate or 1,1-bis(acryloyloxymethyl)ethyl isocyanate are preferable, 2-acryloyloxyethyl isocyanate or 2-methacryloyloxyethyl isocyanate is more preferable, and 2-acryloyloxyethyl isocyanate is further preferable.

(Dialkylcarbamoyl Chloride)

In the present invention, dialkylcarbamoyl chloride is a compound having a carbamoyl group produced by the reaction of the below-mentioned compound (A) and phosgene. The dialkylcarbamoyl chloride is preferably at least one kind of compound selected from the group consisting of N,N-dimethylcarbamoyl chloride, dihexylcarbamoyl chloride, dibenzylcarbamoyl chloride, dicyclohexylcarbamoyl chloride and di-(2-ethylhexyl)carbamoyl chloride.

In the present invention, the content of dialkylcarbamoyl chloride contained in a (meth)acrylic acid ester compound having an isocyanate group is 0.1 mass % or less, preferably 0.01 mass % or less, and more preferably 0.005 mass % or less. There is no particular limitation on the lower limit of the content of dialkylcarbamoyl chloride, which may also be 0 mass ppm. However, since it is not practical to carry out excessive refining from the perspective of yield, the lower limit of the content of dialkylcarbamoyl chloride is, e.g., 1 mass ppm, or may also be 10 mass ppm.

The aforementioned dialkylcarbamoyl chloride content can be measured by gas chromatography in accordance with internal standard methods, e.g., by utilizing a (meth)acrylic acid ester compound having an isocyanate group obtainable via a refining step performed after the below-mentioned step (3). For example, if the content of dialkylcarbamoyl chloride contained in a (meth)acrylic acid ester compound having an isocyanate group before refining is within the aforementioned range, it can be judged that the content of dialkylcarbamoyl chloride contained in a (meth)acrylic acid ester compound having an isocyanate group after refining is also within the aforementioned range.

(N-Disubstituted Formamide Compound (A))

The content of N-disubstituted formamide compound (A) contained in the (meth)acrylic acid ester compound having an isocyanate group of the present invention is preferably 100 mass ppm or less, more preferably 50 mass ppm or less, and furthermore preferably 20 mass ppm or less, from the perspective of stability and easy polymerization of the (meth)acrylic acid ester compound having an isocyanate group. There is no particular limitation on the lower limit of the content of the N-disubstituted formamide compound (A), which may also be 0 mass ppm. However, since it is not practical to carry out excessive refining from the perspective of yield, the lower limit of the content of the N-disubstituted formamide compound (A) is, e.g., 1 mass ppm, or may also be 10 mass ppm.

The N-disubstituted formamide compound (A) has the same meaning as the compound (A) described in the below-mentioned <Method for producing the (meth)acrylic acid ester compound having an isocyanate group>.

The aforementioned (meth)acrylic acid ester compound having an isocyanate group in which the content of dialkylcarbamoyl chloride is 0.1 mass % or less is obtainable by, e.g., the below-mentioned method for production.

<Method for Producing the (Meth)Acrylic Acid Ester Compound Having an Isocyanate Group>

The method for producing the (meth)acrylic acid ester compound having an isocyanate group in which the content of dialkylcarbamoyl chloride is 0.1 mass % or less, which is an embodiment of the present invention, will be explained. This method for production includes step (2) and step (3), and preferably includes step (1). In this method for production, step (3) is performed after step (2), and step (1), if being performed, is performed prior to step (2). Each step is explained as follows.

[Step (2)]

In step (2), a compound (B) and phosgene are brought into contact in the presence of a compound (A) to obtain a phosgene reaction product.

(Compound (A))

Compound (A) is a catalyst employed during the acid-chlorination reaction of compound (B) and phosgene. Compound (A) is N-disubstituted formamide, and is a compound preferably expressed by the following formula (4).

$$NR^1R^2CHO \quad (4)$$

In formula (4), $R^1$ and $R^2$ are each independently an alkyl group having 5 to 10 carbon atoms which may have substituents, a cycloalkyl group having 5 to 10 carbon atoms which may have substituents, or an aryl group having 6 to 10 carbon atoms which may have substituents. However, from the perspective of catalytic activity presumably derived from electronic effect and ease of separation from the (meth)acrylic acid ester compound having an isocyanate group, $R^1$ and $R^2$ are preferably an alkyl group having 6 to 9 carbon atoms which may have substituents, a cycloalkyl group having 6 to 9 carbon atoms which may have substituents, or an aryl group having 7 to 9 carbon atoms which may have substituents. By utilizing the aforementioned compound (A), the content of dialkylcarbamoyl chloride contained in a (meth)acrylic acid ester compound having an isocyanate group can be reduced to 0.1 mass or less. Although this mechanism of action is not known, it is presumed that because the boiling point of dialkylcarbamoyl chloride is high, dialkylcarbamoyl chloride is a residual as a high boiling point component when refining the (meth) acrylic acid ester compound having an isocyanate group by distillation. Examples of the aforementioned substituents include, e.g., an ether group and an aryl group.

The boiling point of compound (A) under atmospheric pressure is preferably 250° C. or more, more preferably 270° C. or more, and furthermore preferably 300° C. or more.

Dihexyl formamide (hereunder referred to as 'DHF'), dibenzyl formamide (hereunder referred to as 'DBNF'), dicyclohexyl formamide (hereunder referred to as 'DCHF') and di(2-ethylhexyl)formamide (hereunder referred to as 'DEHF'), for example, can be preferably utilized in the present invention as compound (A). The boiling point for these in atmospheric pressure are respectively, DHF: 326° C., DBNF: 380° C., DCHF: 329° C., and DEHF: 378° C. Compound (A) is obtainable by the below-mentioned step (1).

(Compound (B))

Compound (B) is a raw material of the (meth)acrylic acid ester compound having an isocyanate group, and is expressed by the following formula (2).

$$R^3\text{—CO—OH} \quad (2)$$

In formula (2), $R^3$ has the same meaning as the $R^3$ of the aforementioned formula (1), and the same also applies to preferred embodiments. (Meth)acrylic acid can be preferably utilized in the present invention as compound (B).

(Conditions)

As long as a phosgene reaction product is obtainable by acid-chlorination of compound (B), there is no particular limitation on the reaction of compound (B) and phosgene, which can be performed under, e.g., the below conditions.

Compound (A) and compound (B) are mixed so that the ratio of compound (A) based on compound (B) is 0.1 to 5.0 mol % per mole of compound (B), and the mixture liquid is heated to 50 to 70° C. 100 to 150 mol % of phosgene per mole of compound (B) is then added, reacted for 1.5 to 3.0 hours at 50 to 70° C., and a phosgene reaction product is thereby obtainable.

During the aforementioned reaction, other components such as polymerization inhibitors may be contained if no adverse effect is imparted to the generation of the phosgene reaction product. Moreover, refining treatment of the phosgene reaction product may be performed by, for example, removal or distillation of the phosgene.

[Step (3)]

In step (3), the phosgene reaction product obtained in the aforementioned step (2) and a hydroxylamine hydrochloride compound are brought into contact to obtain a (meth)acrylic acid ester compound having an isocyanate group expressed by the aforementioned formula (1).

(Hydroxylamine Hydrochloride Compound)

As long as a (meth)acrylic acid ester compound having an isocyanate group expressed by the aforementioned formula (1) is generated by reaction with the phosgene reaction product, there is no particular limitation on the hydroxylamine hydrochloride compound. Examples of the hydroxylamine hydrochloride compound include, e.g., the compound of the following formula (5).

$$(HO)_n\text{—}R^4\text{—}(NH_2)_m(HCl)_m \quad (5)$$

In formula (5), $R^4$, m and n respectively have the same meanings as the $R^4$, m and n of the aforementioned formula (1), and the same also applies to preferred embodiments.

Examples of the hydroxylamine in the hydroxylamine hydrochloride compound include ethanolamine, 3-amino-1-propanol, 2-amino-1-propanol, 1-amino-2-propanol, 4-amino-1-butanol, 2-amino-1-butanol, 2-amino-2-methyl-1-propanol, 5-amino-1-pentanol, 2-amino-1-pentanol, 6-amino-2-methyl-2-heptanol, and 2-(2-amino ethoxy)ethanol. Among these, ethanolamine and 2-(2-amino ethoxy) ethanol can be preferably utilized in the present invention.

(Conditions)

As long as the (meth)acrylic acid ester compound having an isocyanate group of the present invention is obtainable, there is no particular limitation on the reaction of the phosgene reaction product and the hydroxylamine hydrochloride compound, which can be performed by, e.g., known processes. Specifically, hydroxylamine is mixed with a 0.5 to 2.0 mol equivalent of hydrochloric acid per mole of hydroxylamine and is reacted for 0.5 to 2.0 hours at 80 to 100° C. to obtain a hydrochloride of hydroxylamine. 120 to 140 parts by mass of the phosgene reaction product based on 100 parts by mass of the hydrochloride of hydroxylamine is then added and reacted for 0.1 to 1.0 hours to obtain an aminoalkyl acrylate hydrochloride. This and phosgene are brought into contact, reacted for 7 to 10 hours at 80 to 90° C., and an isocyanate group is introduced to the aminoalkyl acrylate hydrochloride to thereby be able to obtain a (meth) acrylic acid ester compound having an isocyanate group.

In the aforementioned reaction, a (meth)acrylic acid ester compound having an isocyanate group obtained by, for example, distillation may also be refined.

The content of the N-disubstituted formamide compound (A) in the (meth)acrylic acid ester compound having an isocyanate group obtained by step (3) is preferably 100 mass ppm or less, more preferably 50 mass ppm or less, and furthermore preferably 20 mass ppm or less, from the perspective of stability and easy polymerization of the (meth)acrylic acid ester compound having an isocyanate group. There is no particular limitation on the lower limit of the content of the N-disubstituted formamide compound (A), which may also be 0 mass ppm. However, since it is not practical to carry out excessive refining from the perspective of yield, the lower limit of the content of the N-disubstituted formamide compound (A) is, e.g., 1 mass ppm, or may also be 10 mass ppm.

The aforementioned N-disubstituted formamide compound (A) content can be measured by gas chromatography in accordance with internal standard methods, e.g., by utilizing a (meth)acrylic acid ester compound having an isocyanate group obtainable via a refining step performed after the below-mentioned step (3). For example, if the content of N-disubstituted formamide compound (A) contained in a (meth)acrylic acid ester compound having an isocyanate group before refining is within the aforementioned range, it can be judged that the content of N-disubstituted formamide compound (A) contained in a (meth) acrylic acid ester compound having an isocyanate group after refining is also within the aforementioned range.

(Step (1))

In step (1), an amine compound of compound (E) expressed by the following formula (3) and formic acid are brought into contact to obtain the aforementioned compound (A).

$$NHR^1R^2 \quad (3)$$

In formula (3), $R^1$ and $R^2$ respectively have the same meanings as the $R^1$ and $R^2$ in the aforementioned formula (4), and the same also applies to preferred embodiments.

(Compound (E))

Dihexylamine, dibenzylamine, dicyclohexylamine, di(2-ethylhexyl)amine, dioctylamine, for example, can be preferably utilized in the present invention as compound (E).

(Conditions)

As long as a compound (A) usable in the present invention is obtainable, there is no particular limitation on the reaction of compound (E) and formic acid, which can be performed by, e.g., known processes. Specifically, compound (E) and an organic solvent are mixed, 1.0 to 1.5 mol equivalent of formic acid per mole of compound (E) is added to the resultant mixture liquid, and reacted for 3 to 6 hours at 100 to 125° C. The reaction liquid after the reaction is filtered, the resultant filtrate is mixed with an organic solvent, to thereby be able to obtain a crystal of compound (A).

The meaning of the terms in the (meth)acrylic acid ester compound having an isocyanate group in which the content of dialkylcarbamoyl chloride is 0.1 mass % or less, in which compound (B) expressed by the aforementioned formula (2) and phosgene are brought into contact in the presence of the aforementioned compound (A) to obtain a phosgene reaction product, and the resultant phosgene reaction product and a hydroxylamine hydrochloride compound are brought into contact to obtain the aforementioned (meth)acrylic acid ester compound having an isocyanate group which is an embodiment of the present invention, has the same meaning as the terms described in the aforementioned <(Meth)acrylic acid ester compound having an isocyanate group> and <Method for producing the (meth)acrylic acid ester compound having an isocyanate group>.

EXAMPLES

The present invention is further specifically explained below based on the Examples; however, the present invention is not restricted to these Examples.

The methods of measurement and calculation in the Examples are as follows.

[Content of 2-Acryloyloxyethyl Isocyanate, Dialkylcarbamoyl Chloride and Catalyst (Formamide Compound)]

The content of 2-acryloyloxyethyl isocyanate, dialkylcarbamoyl chloride and catalyst (formamide compound) were each separated into the respective components by gas chromatography (GC) analysis under the below-mentioned conditions and measured by internal standard methods.

[Hazen color number (APHA)]

The Hazen color number was measured in accordance with JIS K0071-1:2017 with color comparison tubes by comparing them with an APHA reference solution.

[Free Chlorine]

A 10 g sample was measured off in a 100 mL triangle flask, and diluted with methanol to 150 mL. Potentiometric titration was performed on the resultant solution by means of a 1/100 mol/L of a silver nitrate solution to obtain the concentration of free chlorine. The potentiometric titration was carried out by means of an automatic titrator (Product name: COM-550, manufactured by HIRANUMA Co., Ltd.).

[Hydrolyzable Chlorine]

The hydrolyzable chlorine was measured in accordance with JIS K1603:2007 as follows. A 5 g sample was measured off in a 100 mL triangle flask, 35 mL of methanol and 15 mL of water were added to prepare a reaction liquid. A reflux cooler was mounted to this triangle flask, and the reaction liquid was heated under reflux for 30 minutes in an 80° C. water bath, which was then cooled to room temperature. After cooling, potentiometric titration was carried out on the resultant solution by means of 1/100 mol/L of a silver nitrate solution, and the concentration of hydrolyzable chlorine was thereby obtained.

[Measurement Conditions of Gas Chromatography]

Column: Inner diameter of 0.32 mm, length of 30 m, liquid phase film thickness of 1.0 μm (Product name: DB-1, manufactured by J&W Scientific)

Column temperature: Initial temperature 50° C., thereafter temperature was raised by 10° C./minute, final temperature 300° C. (15 minutes)

Inlet temperature: 300° C.

Detector temperature: 300° C.

Detector: Flame ionization detector (FID)

Carrier gas: Helium

Flow rate (column): 1.2 mL/minute

[Producing Rate of Dialkylcarbamoyl Chloride]

For the producing rate of the dialkylcarbamoyl chloride in step (2) (hereunder referred to as 'dicarbamoyl chloride form'), the number of moles of the dicarbamoyl chloride form was calculated with the content of the dicarbamoyl chloride form measured by gas chromatography and the mass of the solution obtained in step (2), and then calculated by dividing that numerical value by the number of moles of the N-disubstituted formamide utilized in step (2).

<Preparation Example 1> Preparation of DHF

DHF (compound (A)) was prepared as follows in accordance with step (1) of the present invention. 37.1 g (0.2 mol) of dihexylamine (compound (E)) and 43.6 g (0.47 mol) of toluene were charged into a 100 mL three-neck flask equipped with a dropping funnel and a Dean-Stark apparatus, where 11.2 g (0.24 mol) of formic acid was dropped through the dropping funnel over 5 minutes. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out for 5 hours while the water generated through the neutralization reaction was removed out of the reaction system due to the azeotrope with toluene. After distilling out the toluene from the reaction liquid under reduced pressure, the objective DHF was obtained by distillation at 0.1 kPa (absolute pressure) and 150° C. The yield of DHF, based on dihexylamine, was 90%.

<Preparation Example 2> Preparation of DBNF

DBNF (compound (A)) was prepared as follows in accordance with step (1) of the present invention. 39.4 g (0.2 mol) of dibenzylamine (compound (E)) and 43.6 (0.47 mol) of toluene were charged into a 100 mL three-neck flask equipped with a dropping funnel and a Dean-Stark apparatus, where 11.2 g (0.24 mol) of formic acid was dropped through the dropping funnel over 5 minutes. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out for 5 hours while the water generated through the neutralization reaction was removed out of the reaction system due to the azeotrope with toluene. The reaction liquid was filtered by means of Type 5A filter paper as specified in JIS P3801:1995 to remove insoluble matter from the reaction liquid. 50 mL of hexane was added to the filtrate, which was cooled to 5° C. to precipitate crystals out. The precipitated crystals were collected by filtering, and the collected crystals were washed twice with 50 mL of hexane. After washing, the crystals were dried for 6 hours at 40° C. to obtain the objective DBNF. The yield of DBNF, based on dibenzylamine, was 67%.

<Preparation Example 3> Preparation of DCHF

DCHF (compound (A)) was prepared as follows in accordance with step (1) of the present invention. 37.1 g (0.2 mol) of dicyclohexylamine (compound (E)) and 43.6 (0.38 mol) of n-butyl acetate were charged into a 100 mL three-neck flask equipped with a dropping funnel and a Dean-Stark apparatus, where 11.2 g (0.24 mol) of formic acid was dropped through the dropping funnel over 5 minutes. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out for 10 days while the water generated through the neutralization reaction was removed out of the reaction system due to the azeotrope with n-butyl acetate. The reaction liquid was filtered by means of Type 5A filter paper as specified in JIS P3801:1995 to remove insoluble matter from the reaction liquid, and then the n-butyl acetate was distilled under reduced pressure to obtain crystals. The resultant crystals were dissolved in 50 mL of hexane, and cooled to 5° C. to precipitate crystals out. The precipitated crystals were collected by filtering, and washed twice with 10 mL of hexane cooled to 5° C. After washing, the crystals were dried for 6 hours at 40° C. to obtain the objective DCHF. The yield of DCHF, based on dicyclohexylamine, was 36.74.

<Preparation Example 4> Preparation of DEHF

DEHF (compound (A)) was prepared as follows in accordance with step (1) of the present invention. 600 g (2.48 mol) of di(2-ethylhexyl)amine (compound (E)) and 538 g (5.84 mol) of toluene were charged into a 2 L three-neck flask equipped with a dropping funnel and a Dean-Stark apparatus, where 137.3 g (2.98 mol) of formic acid was dropped through the dropping funnel over 2 hours. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out for 5 hours while the water generated through the neutralization reaction was removed out of the reaction system due to the azeotrope with toluene. After distilling out the toluene from the reaction liquid under reduced pressure, the objective DEHF was obtained. The yield of DEHF, based on di(2-ethylhexyl)amine, was 90.

<Preparation Example 5> Preparation of Di-n-Butyl Formamide

Di-n-butyl formamide (hereunder referred to as 'DBF') was prepared as follows, as a comparative example of the compound (A) of the present invention. 25.85 g (0.2 mol) of di-n-butylamine and 43.6 g (0.47 mol) of toluene were charged into a 100 mL three-neck flask equipped with a dropping funnel and a Dean-Stark apparatus, where 11.2 g (0.24 mol) of formic acid was dropped through the dropping funnel for 5 minutes. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out over 5 hours while the water generated through the neutralization reaction was removed out of the reaction system due to the azeotrope with toluene. After distilling out the toluene from the reaction liquid under reduced pressure, the objective DBF was obtained by distillation at 0.1 kPa (absolute pressure) and 120° C. The yield of DBF, based on di-n-butylamine, was 93%.

<Preparation Example 6> Preparation of 4-Formylmorpholine 4-formylmorpholine (hereunder referred to as '4-FM') was prepared as follows, as a comparative example of the compound (A) of the present invention. 17.42 g (0.2 mol) of morpholine and 43.6 g (0.47 mol) of toluene were charged into a 100 mL three-neck flask equipped with a dropping funnel and a Dean-Stark apparatus, where 11.2 g (0.24 mol) of formic acid was dropped through the dropping funnel over 5 minutes. Because heat is produced by neutralization reaction at this time, the internal temperature was maintained at 100° C. or less by a water jacket equipped at the exterior. After completing the charging of formic acid, the internal temperature was raised to 125° C. by an oil bath, and the reaction was carried out for 5 hours while the water generated through the neutralization reaction was removed out of the reaction system due to the azeotrope with toluene. After distilling out the toluene from the reaction liquid under reduced pressure, the objective 4-FM was obtained by distillation at 0.1 kPa (absolute pressure) and 100° C. The yield of 4-FM, based on morpholine, was 91%.

<Example 1> Preparation of 2-Acryloyloxyethyl Isocyanate 2-acryloyloxyethyl isocyanate (hereunder referred to as 'AOI') was prepared as follows in accordance with the method for production of the present invention.

[Step (2)]

70 g (0.97 mol) of acrylic acid (compound (B)), 0.01 g (0.07 mol) of phenothiazine, and 2.73 g (1 mol % based on acrylic acid) of the DEHF (compound (A)) prepared in Preparation Example 4 were added into a 200 mL four-neck flask, and temperature was raised to 60° C. 96.1 g (0.97 mol) of phosgene was introduced to this over 8 hours. After reacting for 2 hours at 60° C., an acid chloride mixture containing 3-chloropropionyl chloride (phosgene reaction product) was obtained (mole ratio of 3-chloropropionyl chloride/acryloyl chloride=6.34). The yield of this mixture was 87.84. Moreover, the producing rate of the dicarbamoyl chloride form was 21.8 mol %. Results are shown in Table 1.

[Step (3)]

70 g (1.15 mol) of 2-amino ethanol was put into a 300 mL four-neck flask equipped with a stirrer, condenser, thermometer and inner tube, and the temperature was raised to 85° C. 40.5 g (1.11 mol) of hydrogen chloride was blown into this at 200 mL/minute, and a hydrochloride of ethanolamine was thereby prepared.

Next, 142.6 g of the aforementioned prepared acid chloride mixture was dropped over 90 minutes into the prepared hydrochloride of ethanolamine, and was reacted for 15 minutes to obtain 3-chloropropionyl ethylamine hydrochloride. 115.5 g (1.17 mol) of phosgene was charged over 6.9 hours into the resultant 3-chloropropionyl ethylamine hydrochloride, and was reacted for 1 hour to obtain 3-chloropropionyl ethyl isocyanate. The resultant 3-chloropropionyl ethyl isocyanate was transferred to a 1000 mL four-neck flask, 260 g (2.82 mol) of toluene and 0.6 g (0.004 mol) of a polymerization inhibitor were added, and the temperature was raised to 40° C.

194 g (1.92 mol) of triethylamine was added to this, temperature was then raised to 75 to 80° C., which was reacted for 8 hours. The triethylamine hydrochloride generated by the reaction was removed by filtering to obtain a coarse AOI solution. The content of the dicarbamoyl chloride form in the coarse AOI was 34 mass ppm. After distilling the toluene out from the resultant coarse AOI solution, a refined AOI was obtained by thin film distillation. Dicarbamoyl chloride forms in the refined AOI could not be detected. Results are shown in Table 1.

Examples 2 to 4 and Comparative Examples 1 to 3

As shown in Table 1, except for respectively changing the catalyst of Example 1 and the amount thereof utilized to the catalysts prepared by Preparation Examples 1 to 3, 5 and 6 and the amounts thereof utilized, the AOIs were prepared similarly to Example 1. Results are shown in Table 1. The lower limits of the catalysts in the AOIs and dialkylcarbamoyl chloride forms detected by means of gas chromatography were each 10 mass ppm. Moreover, the content of the dicarbamoyl chloride form in the coarse AOI in Comparative Example 1 was 0.4 mass-. Therefore, unlike the case of the present invention, the dicarbamoyl chloride form in the coarse AOI produced by the comparative examples was difficult to remove by refining, and it is presumed to be easily remaining as a residual in the refined AOI. A commercially available DMF (manufactured by Kanto Chemical Co., Inc.) was utilized in Comparative Example 1.

Example 5

Except for changing the refining method of Example 1 from thin film distillation to simple distillation, the AOI was prepared similarly to Example 1. Results are shown in Table 1.

TABLE 1

| | | Example 1 | Example 2 | Example 3 | Example 4 | Example 5 |
|---|---|---|---|---|---|---|
| Values in step (2) | Utilized catalyst | DEHF | DBF | DBNF | DCHF | DEHF |
| | Boiling point of catalyst (° C.) | 378 | 326 | 380 | 329 | 378 |
| | Amount of catalyst utilized (mol %) (*1) | 1.0 | 1.0 | 1.0 | 1.0 | 1.0 |
| | Yield of CPC + AC (%) (*2) | 87.8 | 84.6 | 81.2 | 86.5 | 87.8 |
| | Mole ratio of CPC/AC | 6.34 | 6.20 | 3.82 | 7.62 | 6.34 |
| | Producing rate of dicarbamoyl chloride form (mol %) | 21.8 | 20.8 | 5.0 | 10.8 | 21.8 |
| Content and indexes in the refined AOIs | AOI (mass %) | 99.5 | 99.1 | 99.1 | 99.2 | 99.4 |
| | Catalyst (formamide compound; (mass ppm) | N.D. | N.D. | N.D. | N.D. | 20 |
| | Dicarbamoyl chloride form (mass %) | N.D. | N.D. | N.D. | N.D. | N.D. |
| | Free chlorine (mass ppm) | <5 | 19 | 9 | 5 | .10 |
| | Hydrolyzable chlorine (mass ppm) | 115 | 145 | 150 | 128 | 130 |
| | APHA | <10 | <10 | <10 | <10 | <10 |
| Producing yield of AOI (%)(*3) | | 78.1 | 74.7 | 74.5 | 77.2 | 80.8 |

TABLE 1

| | | Comparative Example 1 | Comparative Example 2 | Comparative Example 3 |
|---|---|---|---|---|
| Values in step (2) | Utilized catalyst | DMF | DBF | 4-FM |
| | Boiling point of catalyst (° C.) | 153 | 243 | 240 |
| | Amount of catalyst utilized (mol %) (*1) | 1.0 | 0.75 | 1.5 |
| | Yield of CPC + AC (%) (*2) | 81.8 | 86.1 | 86.1 |
| | Mole ratio of CPC/AC | 5.33 | 5.38 | 4.99 |
| | Producing rate of dicarbamoyl chloride form (mol %) | 69.6 | 28.7 | 44.0 |
| Content and indexes | AOI (mass %) | 98.4 | 99.1 | 99.1 |
| | Catalyst (formamide compound) (mass ppm) | N.D. | 100 | N.D. |

TABLE 1-continued

| | | Comparative Example 1 | Comparative Example 2 | Comparative Example 3 |
|---|---|---|---|---|
| in the refined AOIs | Dicarbamoyl chloride form (mass %) | 0.5 | 0.6 | 0.6 |
| | Free chlorine (mass ppm) | 120 | 19 | 9 |
| | Hydrolyzable chlorine (mass ppm) | 2150 | 783 | 1855 |
| | APHA | <10 | <10 | <10 |
| Producing yield of AOI (%) (*3) | | 73.1 | 74.7 | 74.5 |

CPC: 3-chloropropionyl chloride
AC: acryloyl chloride
(*1): amount utilized based on acrylic acid
(*2): yield based on acrylic acid
(*3): producing yield based on ethanolamine

The invention claimed is:

1. A method for producing a (meth)acrylic acid ester compound having an isocyanate group, wherein the content of dialkylcarbamoyl chloride is 0.1 mass % or less in the (meth)acrylic acid ester compound having an isocyanate group, the method comprising:

a step (2) in which a compound (B) expressed by the following formula (2) and phosgene are brought into contact in the presence of an N-disubstituted formamide compound (A) to obtain a phosgene reaction product; and a step (3) in which the phosgene reaction product obtained in the step (2) and a hydroxylamine hydrochloride compound are brought into contact to obtain a (meth) acrylic acid ester compound having an isocyanate group expressed by the following formula (1), wherein the compound (A) is dihexyl formamide, dibenzyl formamide, dicyclohexyl formamide or di(2-ethylhexyl)formamide, a producing rate of the dialkylcarbamoyl chloride in a solution obtained in step (2) is 21.8 or less, for the producing rate of the dialkylcarbamoyl chloride, the number of moles of the dicarbamoyl chloride form is calculated with the content of the dicarbamoyl chloride form measured by gas chromatography and the mass of the solution obtained in step (2), and then calculated by dividing that numerical value by the number of moles of the N-disubstituted formamide utilized in step (2), $$R^3—CO—OH \quad (2)$$

in formula (2), $R^3$ is an ethylenically unsaturated group having 2 or 3 carbon atoms;

$$(R^3—COO)_n—R^4—(NCO)_m \quad (1)$$

in formula (1), $R^3$ means the same as that of the aforementioned formula (2), $R^4$ is a (m+n)-valent hydrocarbon group having 1 to 7 carbon atoms and may optionally contain an ether group, and m and n each independently represent an integer of 1 or 2.

2. The method for producing the (meth)acrylic acid ester compound having an isocyanate group according to claim 1, wherein the dialkylcarbamoyl chloride is at least one compound selected from the group consisting of N,N-dimethylcarbamoyl chloride, dihexylcarbamoyl chloride, dibenzylcarbamoyl chloride, dicyclohexylcarbamoyl chloride and di-(2-ethylhexyl) carbamoyl chloride.

3. The method for producing the (meth)acrylic acid ester compound having an isocyanate group according to claim 1, wherein the (meth)acrylic acid ester compound having an isocyanate group is 2-acryloyloxyethyl isocyanate, 2-methacryloyloxyethyl isocyanate, 2-(isocyanate ethyloxy)ethyl acrylate, 2-(isocyanate ethyloxy)ethyl methacrylate or 1,1-bis(acryloyloxymethyl)ethyl isocyanate.

4. The method for producing the (meth)acrylic acid ester compound having an isocyanate group according to claim 1, wherein the content of dialkylcarbamoyl chloride in the (meth)acrylic acid ester compound having an isocyanate group is 1 mass ppm or more.

5. The method for producing the (meth)acrylic acid ester compound having an isocyanate group according to claim 1, wherein the method further comprises a step (1) in which a compound (E) expressed by the following formula (3) and formic acid are brought into contact to obtain the compound (A), $$NHR^1R^2 \quad (3)$$

in the formula, $R^1$ and $R^2$ are each independently an alkyl group having 5 to 10 carbon atoms which may have substituents, a cycloalkyl group having 5 to 10 carbon atoms which may have substituents, or an aryl group having 6 to 10 carbon atoms which may have substituents.

6. The method for producing the (meth)acrylic acid ester compound having an isocyanate group according to claim 1, wherein the content of the N-disubstituted formamide compound (A) in the (meth)acrylic acid ester compound having an isocyanate group is 100 mass ppm or less.

* * * * *